US011574532B2

United States Patent
Tseng et al.

(10) Patent No.: US 11,574,532 B2
(45) Date of Patent: Feb. 7, 2023

(54) VISIBLE-LIGHT-IMAGE PHYSIOLOGICAL MONITORING SYSTEM WITH THERMAL DETECTING ASSISTANCE

(71) Applicant: Yun yun AI Baby camera Co., Ltd., Taipei (TW)

(72) Inventors: Chih-Hsin Tseng, Taipei (TW); Shih-Yun Shen, Taipei (TW); Hsin-Yi Lin, Taipei (TW); Kang-Ning Shan, Taipei (TW); Hsueh-Fa Hsu, Taipei (TW); Por-Sau Lin, Taipei (TW); Chien-Yu Chen, Taipei (TW); Tzu Ling Liang, Taipei (TW); Huan-Yun Wu, Taipei (TW); Yu-Chiao Wang, Taipei (TW); Chien-Hui Hsu, Taipei (TW)

(73) Assignee: YUN YUN AI BABY CAMERA CO., LTD., Taipei (TW)

( * ) Notice: Subject to any disclaimer, the term of this patent is extended or adjusted under 35 U.S.C. 154(b) by 116 days.

(21) Appl. No.: 17/138,338

(22) Filed: Dec. 30, 2020

(65) Prior Publication Data
US 2021/0358284 A1    Nov. 18, 2021

(30) Foreign Application Priority Data

May 14, 2020   (TW) .................................. 109116098

(51) Int. Cl.
*G08B 21/02*    (2006.01)
*G01D 21/02*    (2006.01)
(Continued)

(52) U.S. Cl.
CPC ............. *G08B 21/02* (2013.01); *G01D 21/02* (2013.01); *G01K 1/024* (2013.01); *G06T 7/0012* (2013.01);
(Continued)

(58) Field of Classification Search
None
See application file for complete search history.

(56) References Cited

U.S. PATENT DOCUMENTS

| 7,972,266 B2 | 7/2011 | Gobeyn et al. |
| 2019/0205655 A1* | 7/2019 | Matsuoka ............ G06V 10/143 |
| 2019/0246075 A1* | 8/2019 | Khadloya ............. H04N 7/183 |

FOREIGN PATENT DOCUMENTS

| CN | 103576660 A | 2/2014 |
| CN | 104684465 A | 6/2015 |

(Continued)

OTHER PUBLICATIONS

TW Search Report Application No. 109116098, dated Oct. 20, 2020.

*Primary Examiner* — Stuart D Bennett
(74) *Attorney, Agent, or Firm* — Muncy, Geissler, Olds & Lowe, P.C.

(57) ABSTRACT

A visible-light-image physiological monitoring system with thermal detecting assistance is disclosed. The system takes a visible-light image and a thermal image of a body at the same time. A processing unit identifies a body feature of the visible-light image and determines a coordinate of the feature. In a learning mode, an initial temperature of the body feature is determined from the thermal image according to the coordinate of the body feature. After then, a physiological status monitoring mode is executed to monitor the temperature changes of the body feature and output an alarm when the temperature is determined to be abnormal. Therefore, a monitoring accuracy of the visible-light-image physiological monitoring system is increased and avoids transmitting false alarms or no alarms.

14 Claims, 10 Drawing Sheets

(51) Int. Cl.
*G06T 7/00* (2017.01)
*G01K 1/024* (2021.01)
*H04N 5/33* (2006.01)

(52) U.S. Cl.
CPC ............... *G06T 2207/20081* (2013.01); *G06T 2207/30196* (2013.01); *G06T 2207/30232* (2013.01); *H04N 5/33* (2013.01)

(56) References Cited

FOREIGN PATENT DOCUMENTS

| | | | | |
|---|---|---|---|---|
| CN | 206060931 U | * | 3/2017 | |
| TW | 384250 | | 3/2000 | |
| TW | 202011268 A | | 3/2020 | |
| WO | WO-2014012070 A1 | * | 1/2014 | ............. A61B 5/015 |

* cited by examiner

|    | Y1  | Y2  | Y3  | Y4  | Y5  | Y6  | Y7  | Y8  |
|----|-----|-----|-----|-----|-----|-----|-----|-----|
| X1 | T11 | T12 | T13 | T14 | T15 | T16 | T17 | T18 |
| X2 | T21 | T22 | T23 | T24 | T25 | T26 | T27 | T28 |
| X3 | T31 | T32 | T33 | T34 | T35 | T36 | T37 | T38 |
| X4 | T41 | T42 | T43 | T44 | T45 | T46 | T47 | T48 |

*FIG. 8*

VISIBLE-LIGHT-IMAGE PHYSIOLOGICAL MONITORING SYSTEM WITH THERMAL DETECTING ASSISTANCE

CROSS-REFERENCE TO RELATED APPLICATIONS

This application is based upon and claims priority under 35 U.S.C. 119 from Taiwan Patent Application No. 109116098 filed on May 14, 2020, which is hereby specifically incorporated herein by this reference thereto.

BACKGROUND OF THE INVENTION

1. Field of the Invention

The present invention is related to a visible-light-image physiological monitoring system, and more particularly to a visible-light-image physiological monitoring system with thermal detecting assistance.

2. Description of the Prior Arts

At present, many image monitoring devices or systems have come out to provide remote user real images at local. With the advancement of image processing technology, the image monitoring devices or systems can identify any human body shown in the images and further analyzes the human body's motion. Therefore, the remote user does not necessarily monitor the images from the image monitoring devices or systems to watch people's activities at local.

In a baby monitoring application, a baby monitor is placed in baby's room and an alarm device linking the baby monitor is portable for parents. The parents can watch the baby through the alarm device. The alarm device further has an alarming function with identification means to help the parents determine whether the baby on the bed may be in danger and quickly remove the danger matter. For example, when the quilt covers the baby's mouth and nose to cause difficulty breathing of the baby, the alarm device analyzes the baby's photo-images from the baby monitor to determine that the quilt covers the baby's mouth and nose. However, in different situations, such as vomiting milk or having a fever, the alarm device can not determine these dangerous situations for the baby by analyzing the baby's photo-images. Therefore, when the parents rely on the baby monitor excessively and the baby monitor can not determine most dangerous situations caused the baby's death, it is a high risk for baby care by using the conventional baby monitor.

To overcome the shortcomings, the present invention provides a visible-light-image physiological monitoring system with thermal detecting assistance to mitigate or to obviate the aforementioned problems.

SUMMARY OF THE INVENTION

An objective of the present invention is to provide a visible-light-image physiological monitoring system with thermal detecting assistance.

To achieve the objective as mentioned above, the visible-light-image physiological monitoring system with thermal detecting assistance has:
  a casing;
  a visible-light image sensor mounted on the casing and outputting multiple visible-light images of a body;
  a thermal sensor movably mounted on the casing and outputting multiple thermal images, wherein a resolution of the thermal image is less than that of the visible-light image;
  a first communication module mounted in the casing; and
  a processing unit mounted in the casing and electrically connected to the visible-light image sensor and the thermal sensor to receive the visible-light images and the thermal images, and controlling the thermal sensor to move relative to the casing, wherein the processing unit identifies multiple features of the body from the visible-light images and determines multiple coordinates of the features through a deep-learning module; the processing unit is electrically connected to the first communication module to transmit a physiological monitoring alarm through the first communication module; and the processing unit has a physiological status determining procedure having:
    a learning mode generating an initial temperature of the at least one feature of the body; and
    a physiological status monitoring mode continuously receiving the visible-light images, and continuously receiving the thermal images of the at least one feature of the body from the thermal sensor after the thermal sensor is controlled to move and to correspond the at least one feature of the body; determining a temperature of the at least one feature from the received thermal images corresponding to the at least one feature according to the initial temperature and the coordinate of the least one feature; and transmitting the physiological monitoring alarm when the temperature is determined to be an abnormal temperature.

With the foregoing description, the visible-light-image physiological monitoring system of the present invention receives the visible-light images of the body and the thermal images of the feature of the body at the same time. The present invention uses the deep-learning module to accurately identify the at least one feature of the body and the coordinates thereof. Furthermore, the processing unit controls the thermal sensor to correspond a position of the feature of the body according to the corresponding feature to receive the thermal image of the feature. Therefore, the processing unit executed the learning mode to identify the features of the body and multiple coordinates of the features and further obtains the body's initial temperature from the thermal image according to the at least one feature and the coordinate thereof. The physiological status monitoring mode is then executed to monitor one of the feature's temperature changes. The physiological monitoring alarm will be transmitted if the temperature is determined to be abnormal. Therefore, the present invention can set a real normal temperature of the body to be monitored as the initial temperature, and accurately monitors the temperature variation of the body's specific feature to reduce the chance of false alarms.

Other objectives, advantages and novel features of the invention will become more apparent from the following detailed description when taken in conjunction with the accompanying drawings.

BRIEF DESCRIPTION OF THE DRAWINGS

FIG. 8 is a pixel chart of an image area of FIG. 5B showing temperatures thereof;

DETAILED DESCRIPTION OF THE PREFERRED EMBODIMENTS

With multiple embodiments and drawings thereof, the features of the present invention are described in detail as follows.

Figure 1:
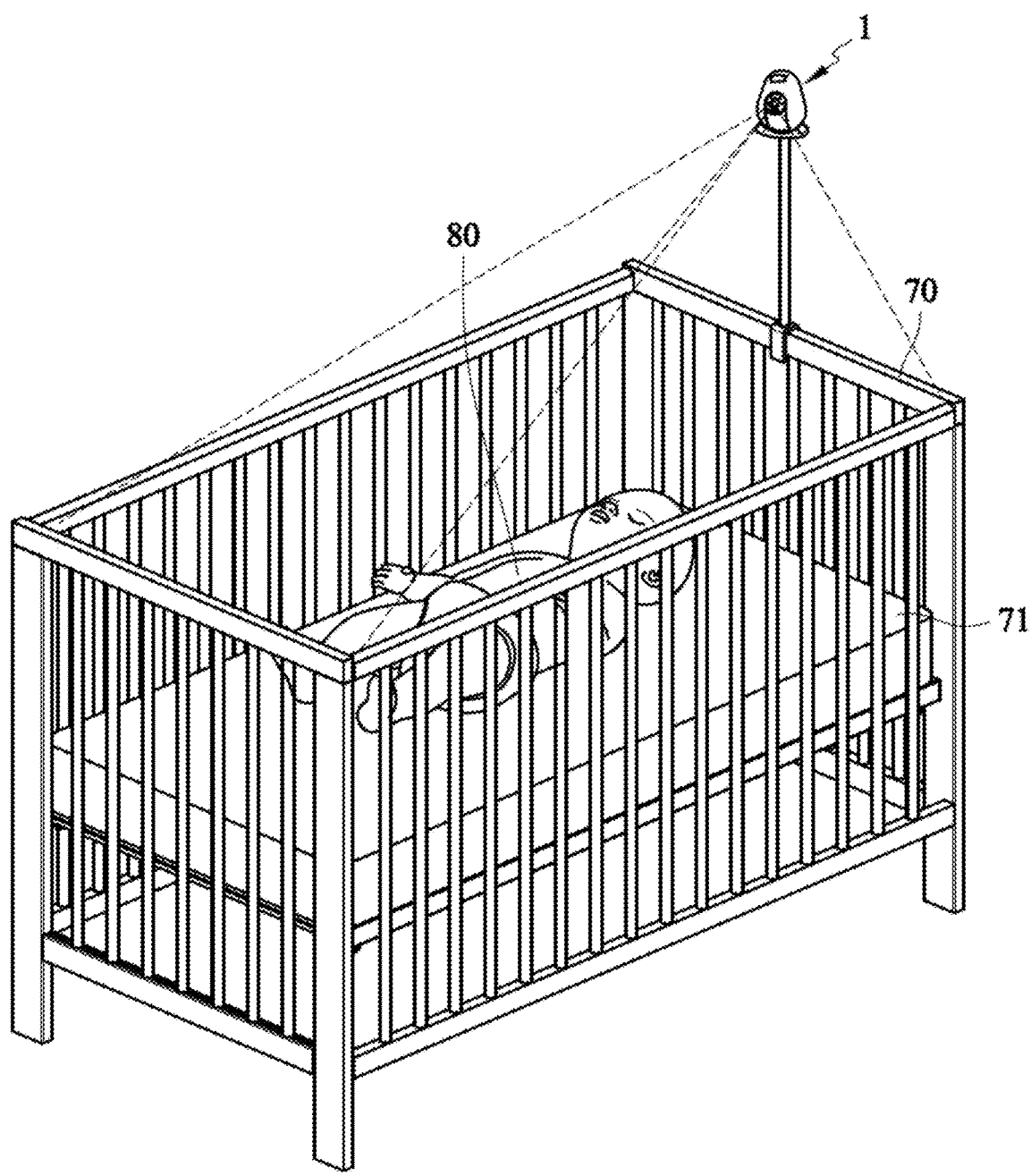
FIG. 1 is a schematic view of a visible-light-image physiological monitoring system mounted to a bedside in accordance with the present invention.
Figure 2:
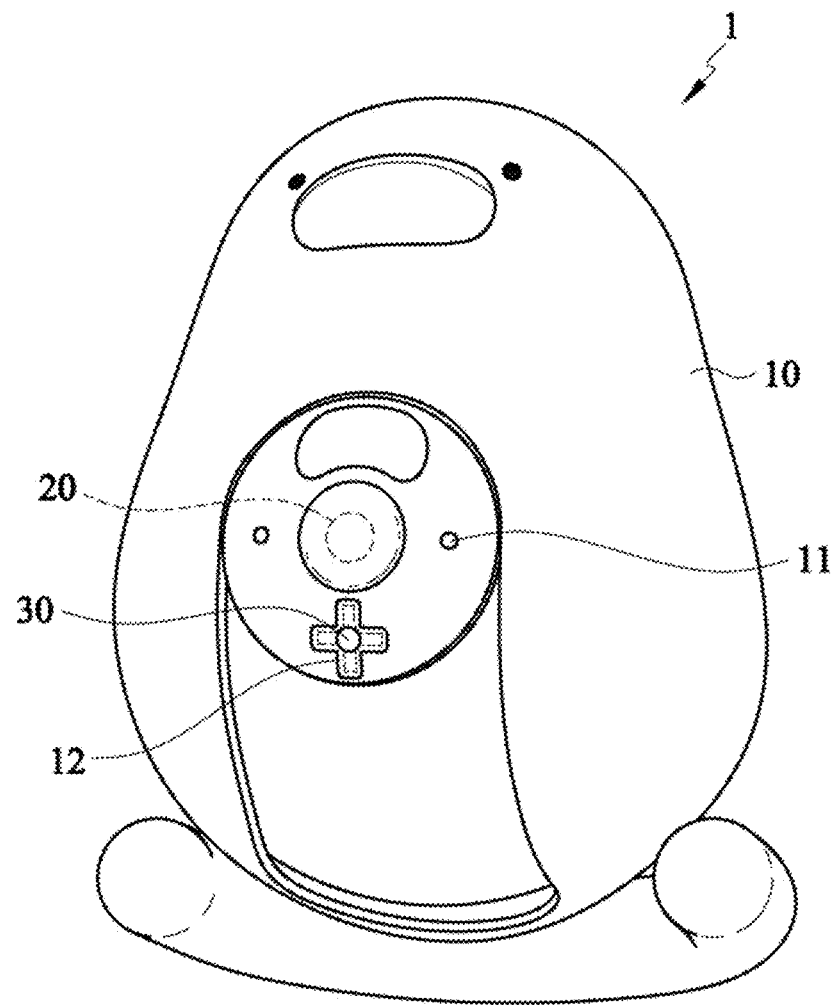
FIG. 2 is a perspective view of the visible-light-image physiological monitoring system in accordance with the present invention.
Figure 4A:
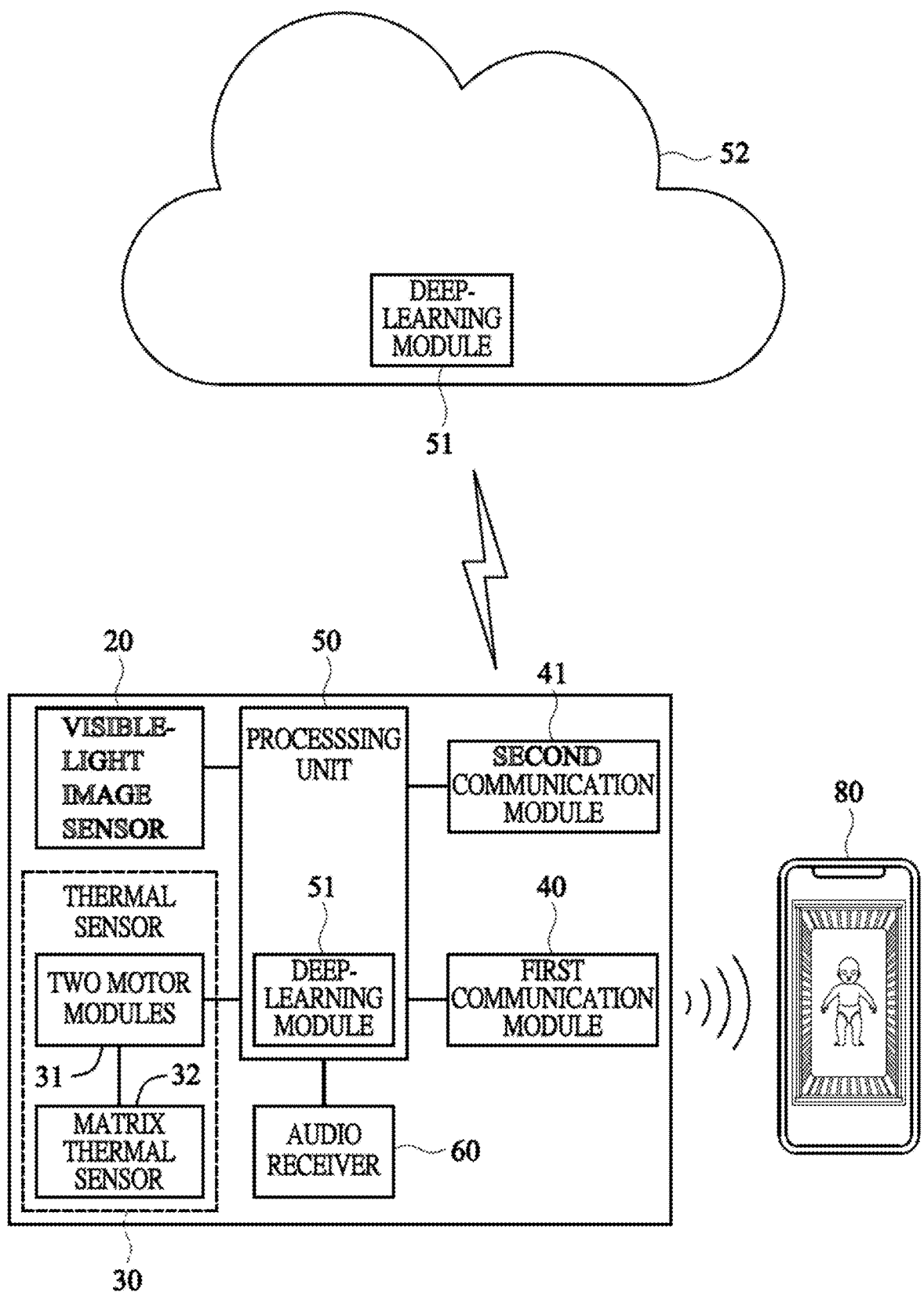
FIG. 4A is a functional block diagram of a first embodiment of the visible-light-image physiological monitoring system in accordance with the present invention.

With reference to FIG. 1, a visible-light-image physiological monitoring system 1 of the present invention is a fixed system so the system may be mounted on a bedside 70 or around a bed to monitor different physiological states of a body 80 on the bed. With further reference to FIGS. 2 and 4A, the system 1 has a casing 10, a visible-light image sensor 20, a thermal sensor 30, a first communication module 40, a processing unit 50 and an audio receiver 60.

In the preferred embodiment, at least one through hole 11 is formed through the casing 10 and a dual-shaft moving device 12 is mounted in the casing. The audio receiver 60 receives an environmental audio from the through hole 11 and outputs an audio signal.

Figure 3:
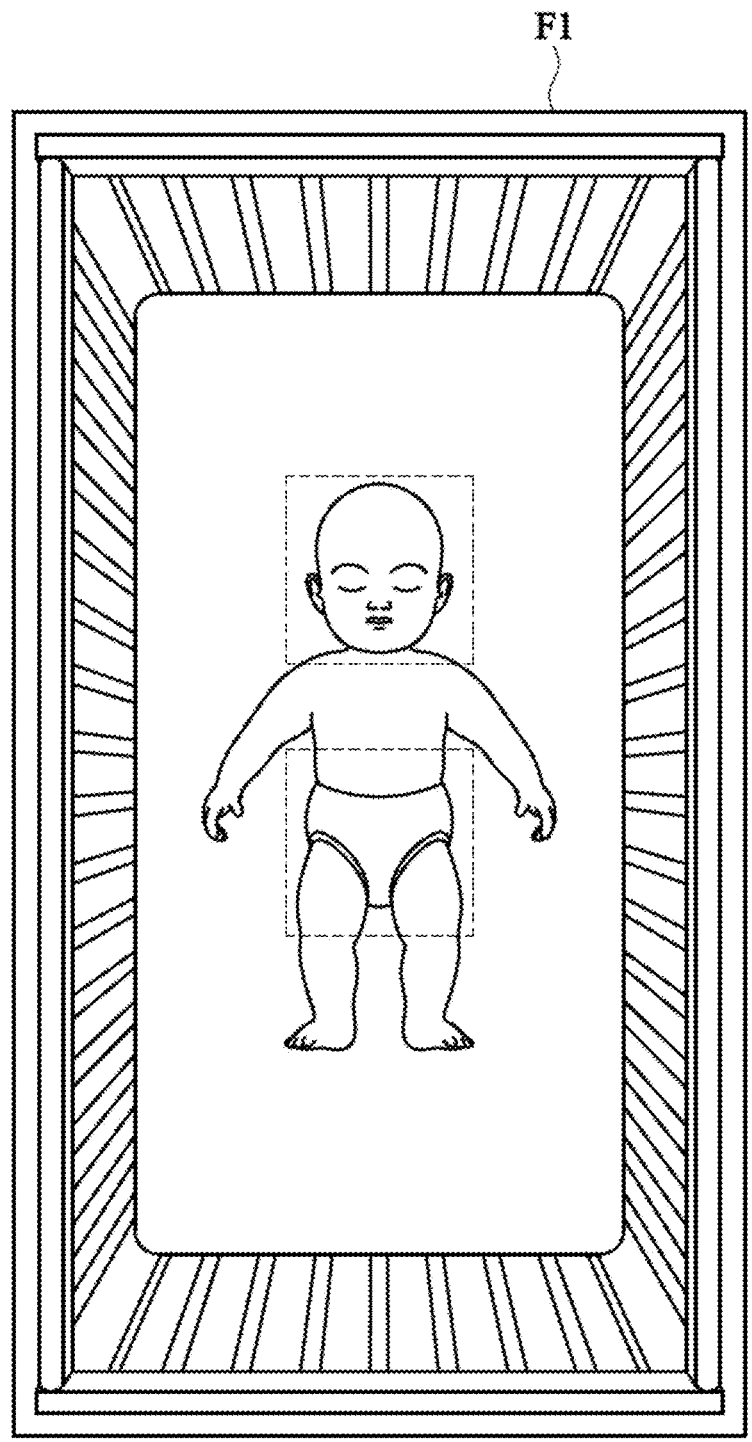
FIG. 3 is a schematic view of one visible-light image.

The visible-light image sensor 20 is mounted on the casing 10 and outputs a visible-light image F1, as shown in FIG. 3. The visible-light image sensor 20 aims to the bed and a shooting range of the visible-light image sensor 20 covers a bed surface 71 of the bed. When a body in the bed, the visible-light image sensor 20 outputs the visible-light image F1 of the body.

Figure 4B:
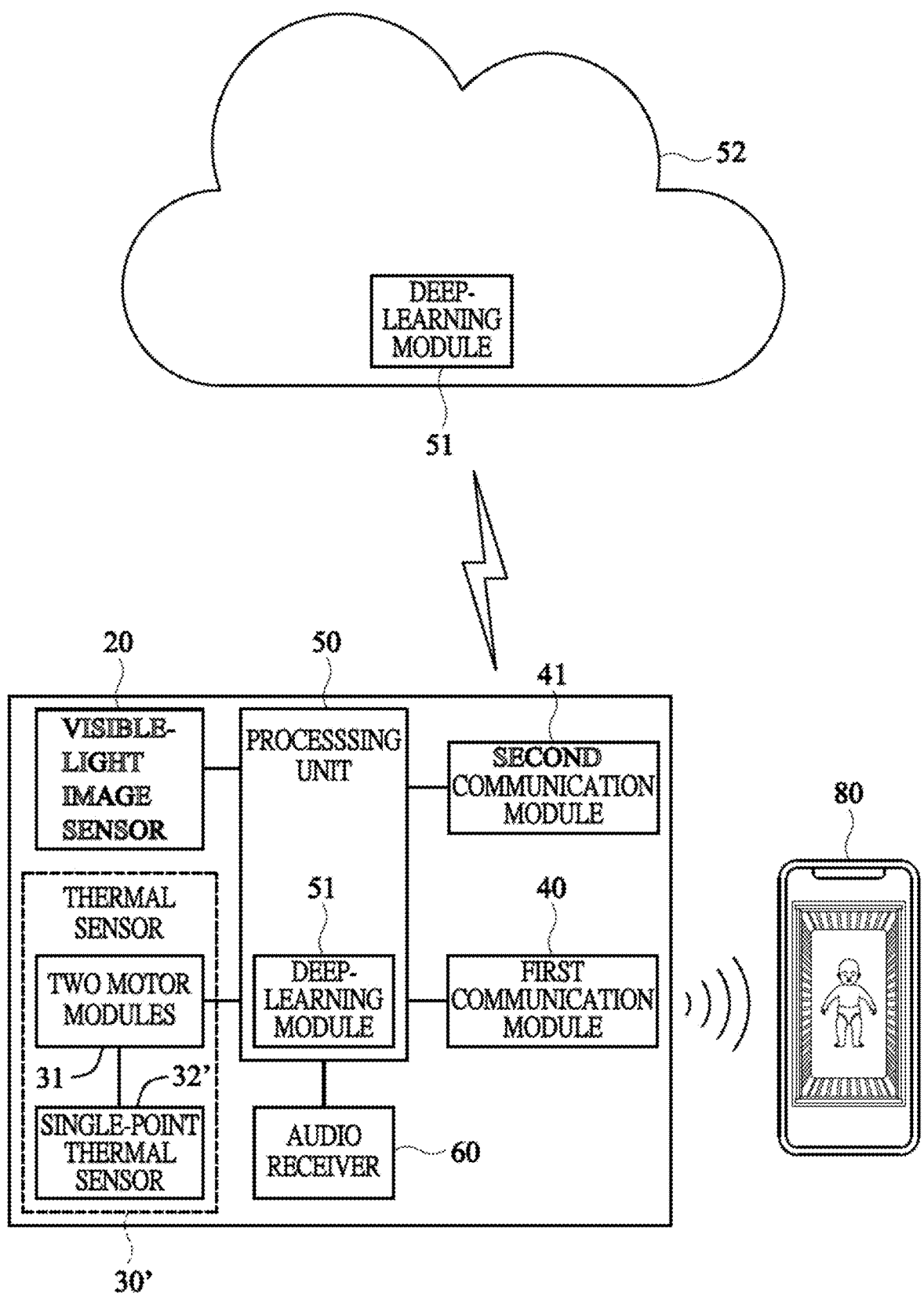
FIG. 4B is a functional block diagram of a second embodiment of the visible-light-image physiological monitoring system in accordance with the present invention.
Figure 5A:
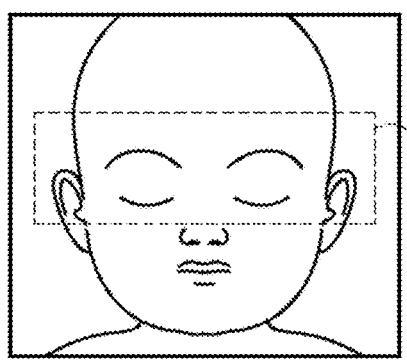
FIGS. 5A and 5B are a partial visible-light image and a thermal image corresponding to the partial visible-light image in accordance with the present invention.
Figure 5B:
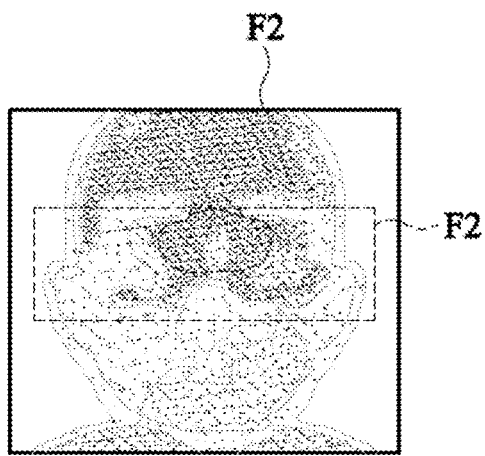

The thermal sensor 30 is movably mounted on the casing 10 and outputs a thermal image F2, as shown in FIG. 5B. In the preferred embodiment, the thermal sensor 30 is a matrix thermal sensor 32 so the thermal image F2 outputted from the thermal sensor 30 has multiple pixels. Each of the pixel contains a temperature value. In one embodiment, a resolution of the thermal image F2 is less than that of the visible-light image F3. As shown in FIGS. 2 and 4A, since the thermal sensor 30 is mounted on the dual-shaft device 12, two motor modules 31 are further connected to the dual-shaft device 12 and electrically connected to the processing unit 50. According to the coordinate of the feature, the processing unit 50 drives the two motor modules 31 to move the dual-shaft device 12 and the matrix thermal sensor 32 relative to the casing 10. Therefore, the matrix thermal sensor 32 is moved to correspond one of feature of the body according to the coordinate of the feature and then output the thermal image of the corresponding feature of the body. With further reference to FIG. 4B, a second embodiment of a visible-light-image physiological monitoring system 1 of the present invention is shown. The visible-light-image physiological monitoring system is similar to that of FIG. 4A, but a thermal sensor 30' is a single-point thermal sensor 32'. The two motor modules 31 are electrically connected to the processing unit 50 and connected to the dual-shaft moving device 12 of the casing 10. The processing unit 50 drives the two motor modules 32 to move the dual-shaft moving device 12 and the thermal sensor 30' on the casing 10. Therefore, the thermal sensor 30' is moveable relative to the casing 10, so a sensing direction of the thermal sensor 30' is adjustable. In particular, the single-point thermal sensor 32' aims and scans the feature of the body and then outputs the thermal image F2 of the at least one feature.

The first communication module 40 is mounted in the casing 10. In one embodiment, the first communication module 40 matches a wireless communication device 72, such as WIFI or Bluetooth, etc.

The processing unit 50 is mounted in the casing 10 and electrically connected to the visible-light image sensor 20, the thermal sensor 30 and the audio receiver 60 to receive the visible-light image F1, the thermal image F2 and the audio signal. In one embodiment, the processing unit 50 may be an AI processor having a built-in deep-learning module 51. The deep-learning module 51 identifies a plurality of the body's features from the visible-light image and further determines a coordinate of each feature. The processing unit 50 is electrically connected to the first communication module 40 and transmits a physiological monitoring alarm to the wireless communication device 72 through the first communication module 40. In one embodiment, the visible-light-image physiological monitoring system further has a cloud server 52. The processing unit 50 may link the cloud server 52 through a second communication module 41. The processing unit 50 may upload the received visible-light images to the cloud server 52. The cloud server 52 has a deep-learning module 51 to identify the plurality of features of the body from the received visible-light images and the features' coordinates. The cloud server 52 sends the processing unit 50 the identified features and the determined coordinates thereof. The processing unit 50 further has a physiological status determining procedure having a learning mode and a physiological status monitoring mode. The processing unit 50 further determines a decibel value of the received audio signal from the audio receiver 60.

Figure 9A:
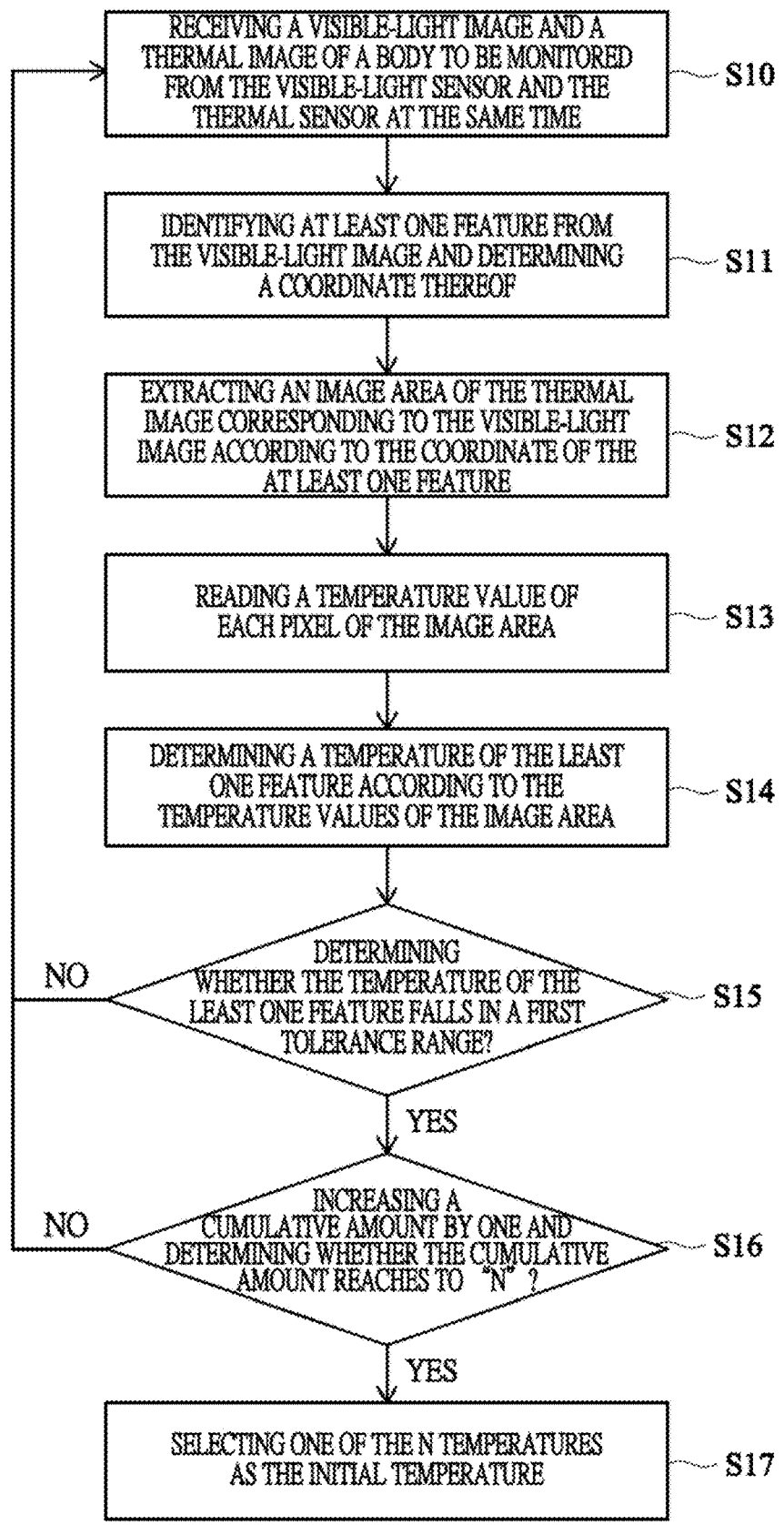
FIG. 9A is a flow chart of a learning mode in accordance with the present invention.

The learning mode generates an initial temperature of at least one feature of the body to be monitored, as shown in FIG. 9A. The learning mode has following steps of S10 to S17.

In the step S10, with reference to FIGS. 3 and 5B, the visible-light image F1 and the thermal image F2 of the body to be monitored are obtained from the visible-light image sensor 20 and the thermal sensor 30 at the same time.

In the step S11, at least one feature of the body to be monitored is identified from the visible-light image F1 and the coordinate of each feature is determined. In one embodiment, with reference to FIGS. 5A, 6A and 7A, the at least one feature of the body to be monitored may include a first feature F11, a second feature F12 and a third feature F13. The first feature F11 contains the area of the eyes and a vicinity thereof. The second feature F12 contains the area of the mouth and a vicinity thereof. The third feature F13 contains the area of a butt and a vicinity thereof.

In the step S12, at least one of the image areas F21, F22 and F23 of the thermal image F2 corresponding to the visible-light image are extracted according to the coordinate of the at least one of the features F11, F12 and F13. With reference to FIGS. 5A and 5B, the coordinates of the first feature F11 of the visible-light image F1 are determined by the deep-learning module 51. The image area corresponding to the first feature is determined from the thermal image F2 according to the first feature F11. Each pixel of the image area has one temperature value. With reference FIGS. 6A and 6B, the second feature F12 of the visible-light image F1 are determined by the deep-learning module 51. The image area F22 corresponding to the second feature F12 is determined from the thermal image F2 according to the coordinates of the second feature F12. Each pixel of the image area F22 has one temperature value. With reference FIGS. 7A and 7B, the coordinates of the third feature F13 of the visible-light image F1 are determined by the deep-learning module 51. The image area F23 corresponding to the third feature F13 is determined from the thermal image F2 according to the coordinates of the third feature F13. Each pixel of the image area F23 has one temperature value.

In the step S13, the temperature values of the image areas F21, F22 and F23 are read. For example, as shown in FIG. 8, the temperature values of all pixels of the image area F21 of FIG. 5B are shown.

In the step S14, a temperature of the at least one feature is determined according to the temperature values of the image areas F21, F22 and F23. In one embodiment, a maximum of the temperature values of each image area F21, F22 or F23 is selected to be represented as the temperature of the corresponding feature. In one embodiment, the temperature values of all pixels of each image areas F21, F22 or F23 are summed and averaged as the temperature of the corresponding feature in this step.

In the step S15, a temperature of the at least one feature is determined whether falls in a first tolerance range. If so, then in the step S16, a cumulative amount is increased by one and the cumulative amount is determined whether reaches N. If the temperature of the at least one feature is determined as not falling in the first tolerance range or the cumulative amount is determined as not reaching N, the steps S10 to S14 are repeated. If the cumulative amount is determined as reaching N in the step S16, the step S17 is then executed to determine one of the temperatures falling in the first tolerance range as an initial temperature of the corresponding feature of the body to be monitored on the bed.

Figure 9B:
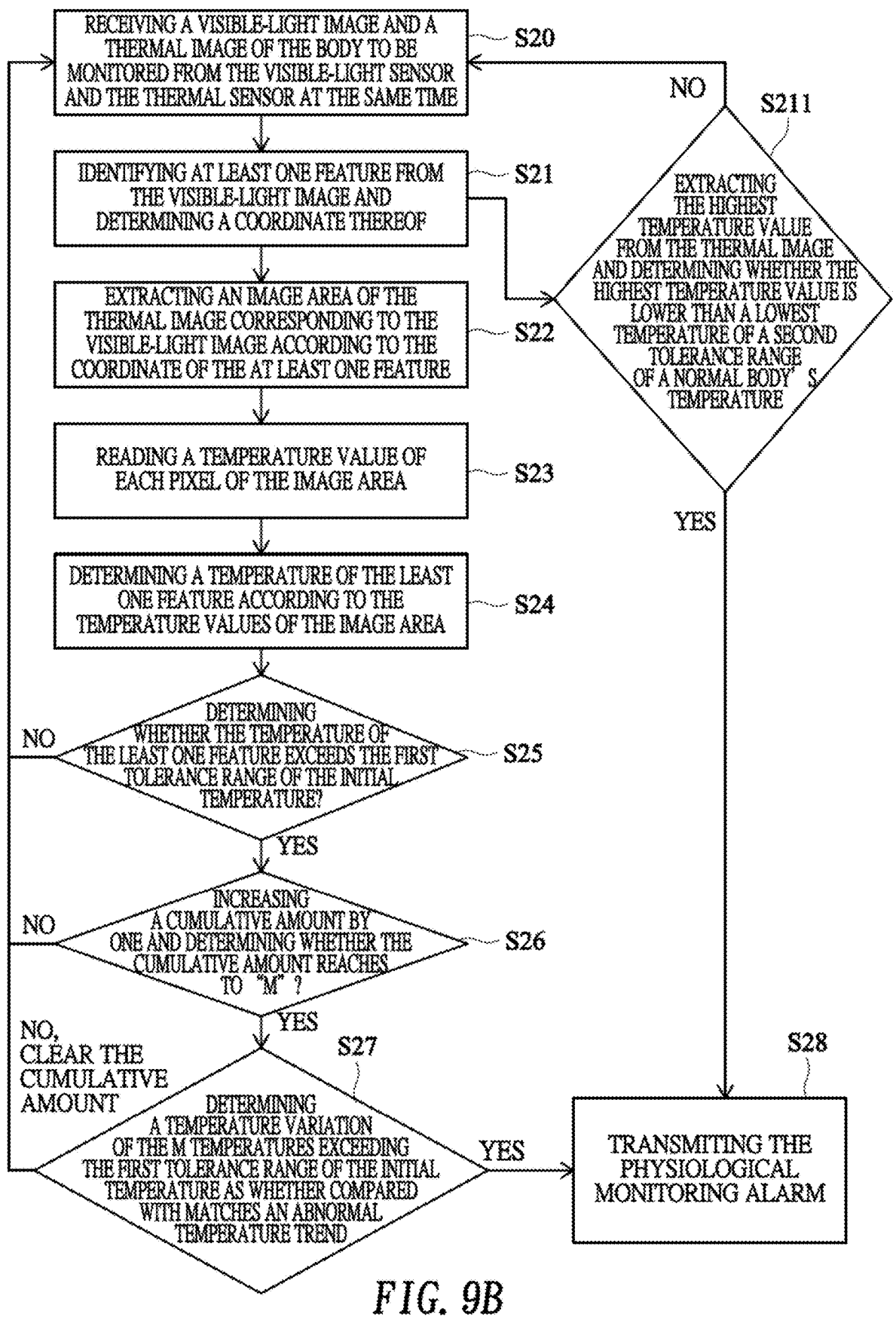
FIG. 9B is a flow chart of a physiological status monitoring mode in accordance with the present invention.

The physiological status monitoring mode is executed after the learning mode is finished. With reference to FIG. 9B, in the physiological status monitoring mode, multiple visible-light images and thermal images are continuously received. A physiological monitoring alarm may be generated when the temperature of the at least one feature is determined as abnormal based on the initial temperature. The physiological status monitoring mode has following steps S20 to S28 and S211.

In the step S20, the visible-light image and the thermal image of the body to be monitored are received from the visible-light image sensor 20 and the thermal sensor 30.

Figure 6A:
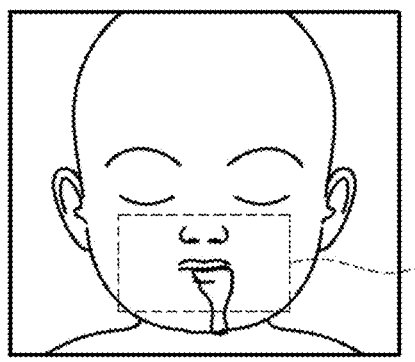
FIGS. 6A and 6B are another partial visible-light image and a thermal image corresponding to the partial visible-light image in accordance with the present invention.
Figure 7A:
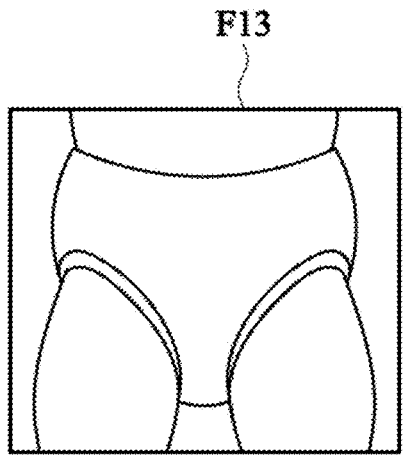
FIGS. 7A and 7B are another partial visible-light image and a thermal image corresponding to the partial visible-light image in accordance with the present invention.

In the step S21, the least one feature and the coordinate thereof are determined from the visible-light image. In one embodiment, as shown in FIGS. 5A, 6A and 7A, the least one feature may include one of the first feature F11, the second feature F12 and the third feature F13. In addition, if no feature of the body to be monitored is identified from the visible-light image in this step, go to the step S211.

In the step S22, at least one image area F21, F22 or F23 of the thermal image F2 corresponding to the visible-light image are extracted according to the coordinate of the at least one feature F11, F12 or F13. With reference to FIGS. 5A, 5B, 6A, 6B, 7A and 7B, the coordinates of the first feature F11, the coordinates of the second feature F12 and the coordinates of the third feature F13 of the visible-light image F1 are determined by the deep-learning module 51. The image areas F21, F22 and F23 corresponding to the above features F11, F12 and F13 are determined from the thermal image F2 according to the coordinates of the features F11, F12 and F13. Each pixel of the image areas F21, F22 and F23 has one temperature value.

In the step S23, the temperature values of the image areas F21, F22 and F23 are read. For example, as shown in FIG. 8, the temperature values of all pixels of the image area F21 of FIG. 5B are shown.

In the step S24, a temperature of the at least one feature is determined according to the temperature values of the image areas F21, F22 and F23. In one embodiment, a maximum of the temperature values of each image area F21, F22 or F23 is selected to be represented as the temperature of the corresponding feature. In one embodiment, the temperature values of all pixels of each image area F21, F22 or F23 are summed and averaged as the temperature of the corresponding feature in this step.

In the step S25, a temperature of the at least one feature is determined whether exceeds a first tolerance range of the initial temperature. If so, then in the step S26, a cumulative amount is increased by one and the cumulative amount is determined whether reaches M. If the temperature of the at least one feature is determined as exceeding the first tolerance range according to the initial temperature or the cumulative amount is determined as not reaching M, the steps S20 to 24 are repeated. If the cumulative amount is determined as reaching M in the step S26, the step S27 is then executed.

Figure 6B:
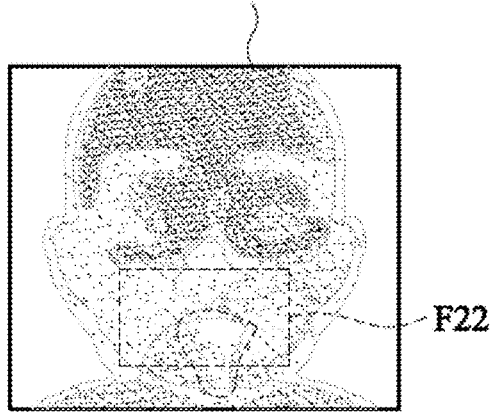
Figure 7B:
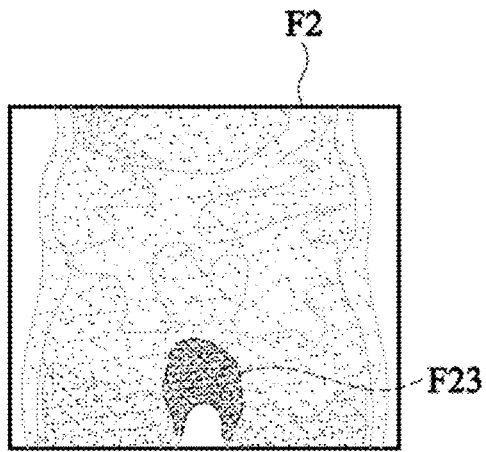
Figure 10A:
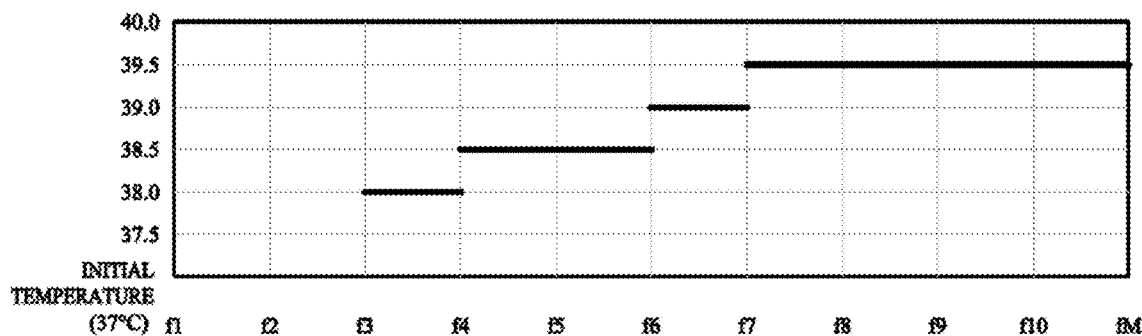
FIGS. 10A to 10D are temperature diagrams of four different monitored statuses in accordance with the present invention.
Figure 10B:
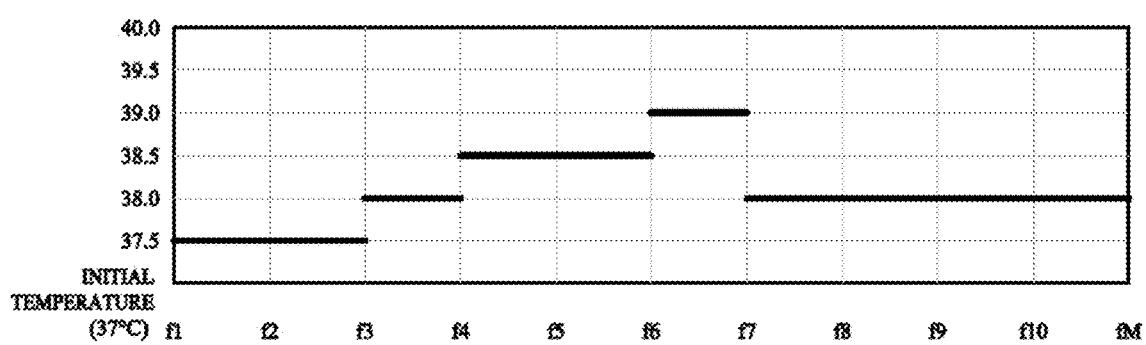
Figure 10C:
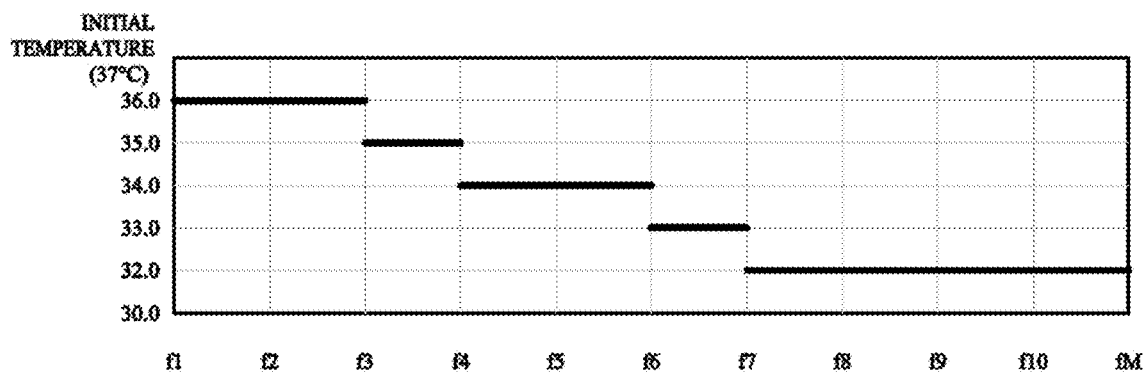
Figure 10D:
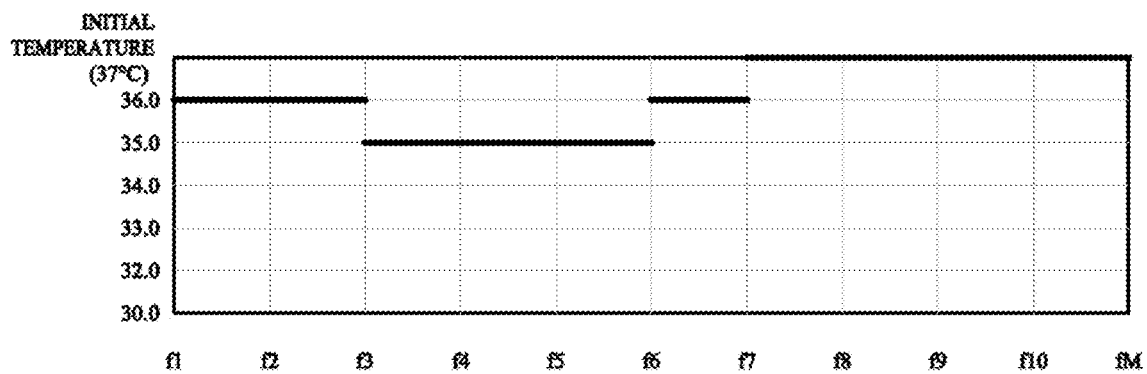

In the step S27, a temperature variation of the temperatures exceeding the first tolerance range of the initial temperature is determined as whether matches an abnormal temperature trend, i.e. a temperature rise rate within a preset period. If matches, go to the step S28. In the step S28, the processing unit 50 transmits the physiological monitoring alarm through the first communication module 40. If not matches, for example, as shown in FIG. 10B, the temperature variation is not going up, go to the step S20. In a baby monitor application (the body to be monitored is a baby's body), as shown in FIGS. 10A and 5B, when the temperature variation is going up, the temperature variation is determined a matching the abnormal temperature trend. It means that the temperature of one part of the baby's body is increased quickly. For example, as shown in FIG. 5B, if the temperature of the first feature is increased quickly, the baby may have a fever and the processing unit 50 transmits a fever alarm. For example, as shown in FIG. 7B, if the temperature of the third feature is increased quickly, the baby may pee or shit on the diaper, the processing unit 50 transmits a diaper alarm. With reference to FIGS. 10C and 6B, if the temperature variation is going down and match another abnormal temperature trend, i.e. a temperature decline rate within a preset period. For example, as shown in FIG. 6B, if the temperature of the second feature is decreased quickly, the baby may vomit milk and the processing unit 50 transmits a milk-vomiting alarm. On the other hand, with reference to FIG. 10D, if the temperature of the second feature is not decreased quickly and the temperature variation does not match the abnormal temperature trend, the processing unit 50 does not determine that the baby vomits milk and go to the step S20.

In addition, in the step S27, if the temperature variation matches the abnormal temperature trend (temperature rise rate within a preset period), the processing unit 50 further calculates the decibel value of the received audio signal from the audio receiver 60 and determines whether the decibel value exceeds a preset decibel value. In the baby monitor application, the body to be monitored is the baby's body and the baby may have a fever and is crying or coughing if the decibel value exceeds the preset decibel value. The processing unit 50 transmits a coughing alarm or crying alarm.

In the step S211, the highest temperature value is extracted from the thermal image. The processing unit 50 determines whether the highest temperature value is lower than a lowest temperature of a second tolerance range of a normal body's temperature. If not, the processing unit 50 transmits the physiological monitoring alarm. In this situation, when the baby is on the bed and the temperature of the body is sensed but not one of the features of the body is identified from the visible-light image, the eyes or mouth of the baby may be covered by something or prone sleeping. The processing unit 50 transmits the physiological monitoring alarm, such as a covered mouth alarm or a prone sleeping alarm. On the other hand, when the highest temperature value is lower than the lowest temperature in a second tolerance range of a normal body temperature, the baby may be not on the bed and the processing unit 50 does not transmit the physiological monitoring alarm.

Based on the foregoing description, the visible-light-image physiological monitoring system of the present invention receives the visible-light images of the body and the thermal images of the feature of the body at the same time. The present invention uses the deep-learning module to accurately identify the at least one feature of the body and the coordinates thereof. Furthermore, the processing unit controls the thermal sensor to correspond a position of the feature of the body according to the corresponding feature to receive the thermal image of the feature. Therefore, the processing unit executed the learning mode to identify the features of the body and multiple coordinates of the features and further obtains the body's initial temperature from the thermal image according to the at least one feature and the coordinate thereof. The physiological status monitoring mode is then executed to monitor one of the feature's temperature changes. The physiological monitoring alarm will be transmitted if the temperature is determined to be abnormal. Therefore, the present invention can set a real normal temperature of the body to be monitored as the initial temperature, and accurately monitors the specific feature's temperature variation by analyzing the specific feature's thermal images, and further determines whether any abnormal temperature change occurs. If the abnormal temperature variation occurs, the processing unit immediately transmits the alarm. Furthermore, the processing unit also analyzes the visible-light images to determine whether any dangerous body action of the baby occurs, such as sleep on all fours, nose or mouth covered by close or quilt. Therefore, the temperature of the baby's body captured by the thermal sensor increases the alarming accuracy of the processing unit in determining such dangerous actions. The processing unit avoids transmitting the false alarms or no alarm.

Even though numerous characteristics and advantages of the present invention have been set forth in the foregoing description, together with the details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A visible-light-image physiological monitoring system with thermal detecting assistance, comprising:
    a casing;
    a visible-light image sensor mounted on the casing and outputting multiple visible-light images of a body;
    a thermal sensor movably mounted on the casing and outputting multiple thermal images, wherein a resolution of the thermal image is less than that of the visible-light image;
    a first communication module mounted in the casing; and
    a processing unit mounted in the casing and electrically connected to the visible-light image sensor and the thermal sensor to receive the visible-light images and the thermal images, and controlling the thermal sensor to move relative to the casing, wherein the processing unit identifies multiple features of the body from the visible-light images and determines multiple coordinates of the features through a deep-learning module; the processing unit is electrically connected to the first communication module to transmit a physiological monitoring alarm through the first communication module; and the processing unit has a physiological status determining procedure having:
    a learning mode generating an initial temperature of the at least one feature of the body; and
    a physiological status monitoring mode having steps of:
        (b1) continuously receiving the visible-light images;
        (b2) identifying at least one feature of the visible-light image and determining a coordinate of each of the at least one feature;
        (b3) controlling the thermal sensor to face a position of the least one feature of the body according to the coordinate of the corresponding feature to continuously receive the thermal images of the at least one feature of the body from the thermal sensor;
        (b4) determining a current temperature of each of the at least one feature from the received thermal images; and
        (b5) transmitting the physiological monitoring alarm when the current temperature is determined to be an abnormal temperature according to the initial temperature.

2. The visible-light-image physiological monitoring system as claimed in claim 1, wherein the learning mode of the physiological status determining procedure has steps of:
    (a1) receiving the visible-light image from the visible-light image sensor and the thermal image from the thermal sensor at the same time;
    (a2) identifying at least one feature of the visible-light image and determining a coordinate of each of the at least one feature;
    (a3) extracting an image area of the thermal image according to the coordinate of the corresponding feature;
    (a4) reading a temperature value of each pixel of the image area;
    (a5) determining a temperature of the feature according to the temperature values of the corresponding image area; and (a6) determining whether the temperature of the feature falls in a first tolerance temperature range, wherein if a determined result is positive, a cumulative amount is increased by one and the cumulative amount is determined whether reaches N, and if the determined result is negative or the cumulative amount is determined as not reaching N, the steps (a1) to (a5) are repeated, wherein if the cumulative amount is determined as reaching N, one of the temperatures falling in the first tolerance range is the initial temperature.

3. The visible-light-image physiological monitoring system as claimed in claim 2, wherein
in the step (a5), a maximum of the temperature values of the image area is selected to be represented as the temperature of the corresponding feature; or
in the step (a5), the temperature values of the image area are summed and averaged as the temperature of the corresponding feature.

4. The visible-light-image physiological monitoring system as claimed in claim 1, wherein the step (b4) of the physiological status monitoring mode comprises:
(b41) extracting an image area of the thermal image according to the coordinate of the corresponding feature;
(b42) reading a temperature values of each pixel of the image area;
(b43) determining a temperature of the feature according to the temperature values of the corresponding image area; and
(b44) determining whether the temperature exceeds the first tolerance range of the initial temperature; wherein if a determining result is positive, a cumulative amount is increased by one and the cumulative amount is determined whether reaches M, and if the determined result is negative or the cumulative amount is determined as not reaching M, the steps (b1) to (b5) and (b41) to (b43) are repeated, wherein if the cumulative amount is determined as reaching M, go to a step (b45); and
(b45) determining whether a temperature variation of the M temperatures matches a normal temperature trend; wherein, if a determining result is positive, the processing unit transmits the physiological monitoring alarm through the first communication module, but if a determining result is negative, go to the step (b1).

5. The visible-light-image physiological monitoring system as claimed in claim 4, wherein in the step (b45), the temperature variation of the M temperatures is a temperature rising trend, and the normal temperature trend is an abnormal temperature rising trend.

6. The visible-light-image physiological monitoring system as claimed in claim 4, wherein in the step (b45), the temperature variation of the M temperatures is a temperature declining trend, and the normal temperature trend is an abnormal temperature declining trend.

7. The visible-light-image physiological monitoring system as claimed in claim 1, wherein the casing further comprises:
a dual-shaft moving device on which the thermal sensor is mounted; and
two motor modules electrically connected to the processing unit and connected to the dual-shaft moving device, wherein the processing unit drives the motor modules to move the dual-shaft moving device along two axis directions.

8. The visible-light-image physiological monitoring system as claimed in claim 7, wherein the thermal sensor is a matrix thermal sensor or a signal-point thermal sensor.

9. The visible-light-image physiological monitoring system as claimed in claim 4, wherein in the step (b2), when no one of the at least one feature of the visible-light image is identified, go to a step of:
(b6) extracting a highest temperature from the thermal image and determining whether the highest temperature is lower than a lowest temperature in a second tolerance range of a normal body temperature, wherein if a determining result is negative, the physiological monitoring alarm is transmitted.

10. The visible-light-image physiological monitoring system as claimed in claim 9, wherein the least one feature is nose or mouth and the physiological monitoring alarm is a covered mouth alarm or a prone sleeping alarm.

11. The visible-light-image physiological monitoring system as claimed in claim 9, wherein the processing unit is further electrically connected to an audio receiver to receive an audio signal and determine a decibel value of the audio signal.

12. The visible-light-image physiological monitoring system as claimed in claim 11, wherein in the step (b45), the decibel value of the audio signal is obtained to further determined whether the decibel value exceeds a preset decibel value, when the temperature variation of the M temperatures matches a normal temperature rising trend; wherein if a determining result is positive, a crying alarm or a coughing alarm is transmitted.

13. The visible-light-image physiological monitoring system as claimed in claim 1, wherein the deep-learning module is built in the processing unit.

14. The visible-light-image physiological monitoring system as claimed in claim 1, further comprising:
a second communication module mounted in the casing and electrically connected to the processing unit; and
a cloud server linking to the processing unit through a second communication module and the deep-learning module is built in the cloud server to identify the at least one feature of the visible-light image and determine the coordinate of each of the at least one feature; wherein the cloud server sends the processing unit the at least one feature of the visible-light image and the coordinate of each of the at least one feature.

* * * * *